US005591767A

United States Patent [19]

Mohr et al.

[11] Patent Number: 5,591,767
[45] Date of Patent: * Jan. 7, 1997

[54] LIQUID RESERVOIR TRANSDERMAL PATCH FOR THE ADMINISTRATION OF KETOROLAC

[75] Inventors: Judy M. Mohr, Menlo Park; Richard W. Baker, Palo Alto; Lisa A. Nakaji, San Jose, all of Calif.

[73] Assignee: Pharmetrix Corporation, Menlo Park, Calif.

[ * ] Notice: The term of this patent shall not extend beyond the expiration date of Pat. No. 5,589,498.

[21] Appl. No.: 470,659

[22] Filed: Jun. 6, 1995

Related U.S. Application Data

[63] Continuation of Ser. No. 10,256, Jan. 25, 1993, abandoned.
[51] Int. Cl.$^6$ .............................. A61K 31/40; A61K 9/70
[52] U.S. Cl. ............................................ 514/413; 424/449
[58] Field of Search ............................ 514/413; 424/449

[56] References Cited

U.S. PATENT DOCUMENTS

| | | | |
|---|---|---|---|
| 3,797,494 | 3/1974 | Zaffaroni | 128/268 |
| 4,031,894 | 6/1977 | Urquhart et al. | 128/268 |
| 4,089,969 | 5/1978 | Muchowski et al. | 424/274 |
| 4,460,372 | 7/1984 | Campbell et al. | 604/897 |
| 4,588,580 | 5/1986 | Gale et al. | 424/21 |
| 4,615,699 | 10/1986 | Gale et al. | 604/897 |
| 4,818,541 | 4/1989 | Sanderson | 424/448 |
| 4,839,174 | 6/1989 | Baker et al. | 424/447 |
| 4,906,463 | 3/1990 | Cleary et al. | 424/78 |
| 4,908,027 | 3/1990 | Enscore et al. | 604/890.1 |
| 4,910,205 | 3/1990 | Kogan et al. | 514/290 |
| 4,915,950 | 4/1990 | Miranda et al. | 424/448 |
| 4,956,181 | 9/1990 | Bayer et al. | 424/448 |
| 4,992,445 | 2/1991 | Lawter et al. | 514/279 |
| 5,008,110 | 4/1991 | Benecke et al. | 424/448 |
| 5,049,386 | 9/1991 | Eppstein et al. | 424/427 |
| 5,069,909 | 12/1991 | Sharma et al. | 424/449 |
| 5,091,182 | 2/1992 | Ong et al. | 424/400 |
| 5,114,946 | 5/1992 | Lawter et al. | 514/279 |
| 5,124,157 | 6/1992 | Colley et al. | 424/448 |
| 5,519,046 | 5/1996 | Noda et al. | 514/413 |

FOREIGN PATENT DOCUMENTS

| | | |
|---|---|---|
| 4-321624 | 11/1992 | Japan . |
| 9103998 | 4/1991 | WIPO . |
| WO93/04677 | 3/1993 | WIPO . |
| WO93/24114 | 9/1993 | WIPO . |

OTHER PUBLICATIONS

Baker, R. W. *Controlled Release of Biologically Active Agents*, John Wiley & Sons, NY pp. 4–10 (1987).
Jamali et al. *J. of Pharmaceutical Sciences* 789 695–714 (1989).
Campbell, D. B. *European J. of Drug Metabolism and Pharmacokinetics*15 109–125 (1990).
Guzman, et al. *J. Med. Chem.* 29 589–591 (1986).
Mroszczak et al. *Clin. Pharmacology & Therapeutics*49 126 (1991).
Stinson *C&EN*46–79 (Sep. 28, 1992).
Yu, et al., "Percutanteous Absorption of Nicardipine and Ketorolac in Rehsus Monkeys," Pharmaceutical Research, vol. 5, No. 7, 1988, pp. 457–462.
Greenwald, "Ketorolac: An Innovative Non–Steroidal Analgesic," Drugs of Today, vol. 28, No. 1, 1992, pp. 41–61.
Pfister, et al., "Permeation Enhancers Compatible with Transdermal Drug Delivery Systems—Part I . . . ," Phar. Tech. Sep. 1990, pp. 132–140.
Brocks et al., *Medline Abstract*No. 93092511, 1992.

*Primary Examiner*—Marianne M. Cintins
*Assistant Examiner*—William R. A. Jarvis
*Attorney, Agent, or Firm*—Townsend and Townsend and Crew

[57] ABSTRACT

The invention is directed to a patch for the transdermal delivery of the racemic form or the active enantiomer of the analgesic ketorolac. The transdermal patch is capable of delivering therapeutically effective doses of the drug for a period of 12 hours or more. The patch is capable of delivering the racemate of ketorolac at a flux rate of 40 µg/cm$^2$·hr or more, and of the active enantiomer at a flux rate of 20 µg/cm$^2$·hr or more.

16 Claims, 3 Drawing Sheets

LIQUID RESERVOIR TRANSDERMAL PATCH FOR THE ADMINISTRATION OF KETOROLAC

This is a continuation of application Ser. No. 08/010,256, filed Jan. 25, 1993, now abandoned.

BACKGROUND OF THE INVENTION

The present invention relates to the transdermal delivery of the active enantiomer or the racemic form of ketorolac from a patch that can deliver a therapeutically effective dose of the drug through the skin of a patient in need of such treatment for an extended period of time of at least 12 hours or more.

Ketorolac is a non-steroidal anti-inflammatory agent with potent analgesic properties. The drug is currently administered as the racemic mixture orally or by injection and is commercially available in forms suited for such modes of delivery. Ketorolac tromethamine salt in sterile water for intramuscular and intravenous administration is available at concentrations ranging from 1.5% (15 mg in 1 ml) to 3% (60 mg in 2 mls). Typically, when injected, a bolus dose of 30 to 60 mg is first given followed by subsequent injections of half the loading dose (15 to 30 mg) every 6 to 8 hours. The total daily doses of the drug as such is in the range of 60–120 mg. Delivered at these levels, the drug is extremely effective. However, the need for repeated injections due to the relatively rapid metabolism of the drug makes this mode of delivery inconvenient in certain situations.

A far more convenient and acceptable form of delivery is simple oral delivery 2 to 3 times per day. However, oral administration of ketorolac can be quite irritating to the gastrointestinal tract. Thus, for oral use, the FDA has approved only low-dosage tablets containing only 10 mg of ketorolac tromethamine salt. Of course patients can take more than one tablet, but in general it is normally not safely possible to maintain the same highly effective blood levels obtained with the injectable form when the drug is given orally.

Thus there is an interest in developing alternative modes of delivering ketorolac which do not have the gastrointestinal side effects produced by oral formulations but which are more convenient than injection methods. Nasal formulations of ketorolac are described in application U.S. Ser. No. 875,700, filed Apr. 29, 1992. In co-pending application U.S. Ser. No. 07/973,801 filed Nov. 9, 1992, now abandoned, the transdermal delivery of the active enantiomer of ketorolac is described.

The use of transdermal patches for drug delivery is particularly beneficial when it is desired to maintain a constant blood level of drug in the patient for extended periods of time. There is an added benefit in that oftentimes, the required dose of a drug when delivered by a 24 hour transdermal patch can be one half or less that of the dose delivered by a single once a day intravenous or oral dose. This is particularly true if the drug has a high clearance value. With conventional drug delivery methods, if a drug has a high clearance value it is necessary to administer a large dose of the drug to extend the time it takes the blood drug levels to fall below the therapeutically effective level. But with transdermal delivery, the dose of a drug with a high clearance value can be lower since the drug is controlled released, and does not have to be administered at levels much greater than the therapeutically effective level.

The concept of clearance is described in detail in Rowland & Tozer's, *Clinical Pharmacokinetics: Concepts and Applications*, (2nd Ed. 1989) [hereinafter Rowland & Tozer]. Briefly, clearance does not indicate how much drug is being removed from the system but, rather, the volume of biological fluid such as blood or plasma that would have to be completely freed of drug to account for the elimination. Clearance is expressed as a volume per unit of time. Clearance by means of various organs of elimination is additive. Elimination of drug may occur as a result of processes that occur in the kidney, liver, and other organs. When the respective clearance by each organ is added together, they equal total systemic clearance.

The half-life of a drug is the amount of time it takes the total level of drug in a body to decrease by 50%. Clearance is related to the half-life of a drug by Equation 1:

$$T_{1/2} = \frac{0.693 \times \text{Volume of distribution}}{\text{Clearance}}$$

The relationship between the conventional dose of a drug and the dose of drug delivered transdermally can be calculated if the half-life of the drug is known. This procedure is described on pages 5–10 of Baker, R. W., *Controlled Release of Biologically Active Agents*, John Wiley and Sons, New York, (1987) [hereinafter Baker]. Using this procedure, the data shown in Table I and FIG. 1 has been calculated.

Table I shows that the ratio of dose required for the transdermal delivery of a drug compared to the dose required for conventional drug delivery decreases as the half-life of the drug decreases. Thus, if the half-life of the drug is 24 hours, then a transdermal patch delivering drug to the body at a relatively constant rate should only have to deliver 84.5% of the dose of a conventional instant dose form of the drug delivered once every 24 hours. In this case, the advantage offered by controlled transdermal delivery is relatively small, only a 15.5% reduction in dose. However, if the half-life of the drug is 4 hours, the approximate half-life of ketorolac, then the advantage offered by constant delivery is much greater compared to conventional delivery given once every 24 hours, namely a reduction in dose of almost 75%. Even if an injectable dose is given every 8 hours, the reduction in dose obtained when a transdermal patch is used is still substantial, being on the order of 40 to 50%.

TABLE I

| Drug Half-life (in hours) | Ratio of dose required of controlled release form compared to conventional form (for a 24-hour device) |
|---|---|
| 24 | 0.845 |
| 12 | 0.595 |
| 6 | 0.350 |
| 4 | 0.250 |
| 3 | 0.205 |

Thus it follows that if the total amount of ketorolac delivered by regular injections three times a day to control pain is approximately 60–120 mg/day, then a 30–60 mg/day dose delivered transdermally would produce approximately the same benefit without the problems of overdosing and underdosing associated with injectable delivery. This type of calculation has lead to interest in delivering ketorolac transdermally. For example, transdermal delivery of ketorolac from nearly saturated solutions in various enhancer combinations has been studied by others (D. Yu et al, *Pharm. Res.* 5(7): 457–462, (1988)). In another study, a 2% ketorolac topical gel was studied (R. Greenwald, *Drugs of Today*, 29(1): p.52, (1992)). The patients applied 3 g of the gel three times per day without occlusion. Serum concentrations of approximately 0.17–0.18 μg/ml were attained, significantly below the generally accepted target level for good analgesia with ketorolac of 0.3 to 5.0 μg/ml.

These dissatisfying results are not surprising. It is well known in the art of transdermal drug delivery that it is very difficult to deliver drugs at a rate of greater than 10–20 μg/cm$^2$·hr. Of the 9 drugs delivered by approved commercial transdermal formulations only two, nicotine and nitroglycerine, both very permeable liquids, deliver drug at this rate. Most of the other formulations deliver the drugs at a much lower rate. It has been proposed that the permeability of skin to a given drug can be correlated with the drug's melting point according to the relationship set forth in FIG. 2 (Baker, supra). Based on this, the expected flux of ketorolac with a melting point of 160° C. would be 0.06 μg/cm$^2$·hr. The expected flux of ketorolac tromethamine, which has melting point similar to that of the free acid, would be about the same.

It follows that if the estimated transdermal dose of 30–60 mg/day of ketorolac is to be delivered by a transdermal device, the area of the patch required would be impossibly large, on the order of 2–4 m$^2$. Of course, skin permeation enhancers could be used to increase the delivery, but if conventional sized patches of the order of 30 cm$^2$ or less are to be used, skin permeation rates from the patch of the order of 42–84 μg/cm$^2$·hr would be required—a very considerable degree of enhancement.

Patch design is governed by several factors: permeability of drug to the skin, dose of drug required, enhancers used to deliver drug, and the flux rate of drug and enhancer required to achieve a therapeutic effect. Accordingly, there is much literature on the design of transdermal patches, with variations on a particular design being influenced by the above factors. Liquid reservoir patches of various designs are well known to researchers in the field of transdermal drug delivery. For example, U.S. Pat. No. 4,460,372 ('372) discloses a transdermal patch having, in order from skin-distal side of patch to skin-facing side of patch, a backing layer, an enhancer reservoir layer containing a solvent type enhancer such as ethanol, a diffusion membrane layer, and a drug reservoir-contact adhesive layer. In this patent, a rate-controlling membrane separates an enhancer reservoir from the drug depot rather than having the enhancer and drug within the same compartment. The premise is that the drug delivered does not need the rate-controlling effect of the diffusion membrane layer, whereas the enhancer does. Without the diffusion membrane layer, the flux of the enhancer would be too high. However, if the drug were to pass through the diffusion membrane layer, its flux would be too low to achieve a therapeutic effect.

In U.S. Pat. No. 4,379,454, a patch somewhat similar to the '372 patch is described. The difference with this patch is that both the drug and the solvent enhancer are contained in the reservoir layer and are separated from the skin by a microporous membrane. The membrane is quite permeable to the drug which is able to permeate the membrane at a rate higher than the skin's ability to absorb the drug. However, the membrane is relatively less permeable to the enhancer. As a result, the enhancer permeates the membrane, and subsequently the skin, at a rate less than the skin's ability to absorb the enhancer. The membrane is thus a rate controlling barrier for the enhancer. When this type of patch is used to deliver drug, the rate of absorption of the drug can be controlled mostly by the permeability of the membrane to the enhancer. If the membrane is relatively impermeable to the enhancer, the rate of delivery of enhancer to the skin will be low and the enhancement effect achieved will also be low. This will result in a low drug absorption rate. Correspondingly if the permeability of the membrane to enhancer is high, the rate of delivery of enhancer to the skin will also be high as well as the resulting enhancement effect achieved. This will result in a high drug absorption rate. The difficulty with these types of devices is that they require precise control of the enhancers permeability through the membrane to achieve good control of drug absorption. In practice, this level of control is difficult to achieve.

U.S. Pat. No. 4,031,894 describes another type of transdermal patch having an impermeable backing layer, a layer of drug gelled in mineral oil, a microporous membrane, and a contact adhesive layer containing drug. The drug in the contact adhesive layer is the "pulse dosage" which rapidly permeates through the patient's skin. Thereafter the delivery rate of the drug is controlled by the microporous membrane.

European patent application 0 413 487 A1 discloses a transdermal patch for the delivery of dexmedetomidine. It comprises (from skin distal to skin-facing side) a backing layer, an adhesive layer, a porous intermediate layer, a drug/contact adhesive layer, and a release liner. The porous intermediate layer functions as structural reinforcement and can be made of a non rate-controlling, nonwoven fabric such as polyester. Upon fabrication, the anchor adhesive and contact adhesive migrate into the intermediate layer.

None of the above references disclose a transdermal patch design that is useful in delivering therapeutic amounts of ketorolac. Accordingly, it is an object of this invention to provide a transdermal patch that can deliver ketorolac at a rate that attains a therapeutic level.

Another object of the present invention is to provide a ketorolac transdermal patch that is less than 30 cm$^2$ in active surface area.

It is a further object of the invention to provide a transdermal ketorolac patch that avoids or minimizes skin irritation.

Another object of the invention is to provide a ketorolac transdermal patch that is effective in providing analgesia for periods of 12 hours or more.

These and other objects and features of the invention will be apparent to those skilled in the art from the following detailed description and appended claims when taken in conjunction with the figures.

SUMMARY OF THE INVENTION

A patch for the transdermal administration of ketorolac is described. The patch is capable of delivering therapeutically effective levels of ketorolac through a patient's skin for a period of 12 hours or more. The patch is a reservoir type and comprises an occlusive backing layer and a porous membrane which are sealed together at their peripheral edges defining a drug depot containing ketorolac and an enhancer. The patch is capable of delivering ketorolac through a patient's skin at flux rates of about 40 μg/cm$^2$·hr or more.

A method of administering ketorolac is also described. The method comprises applying a transdermal patch to the skin of a patient in need of ketorolac, said patch containing ketorolac and an enhancer, and delivering ketorolac through the patient's skin at a flux rate of about 40 μg/cm$^2$·hr or more.

DESCRIPTION OF THE PREFERRED EMBODIMENTS

Figure 1:
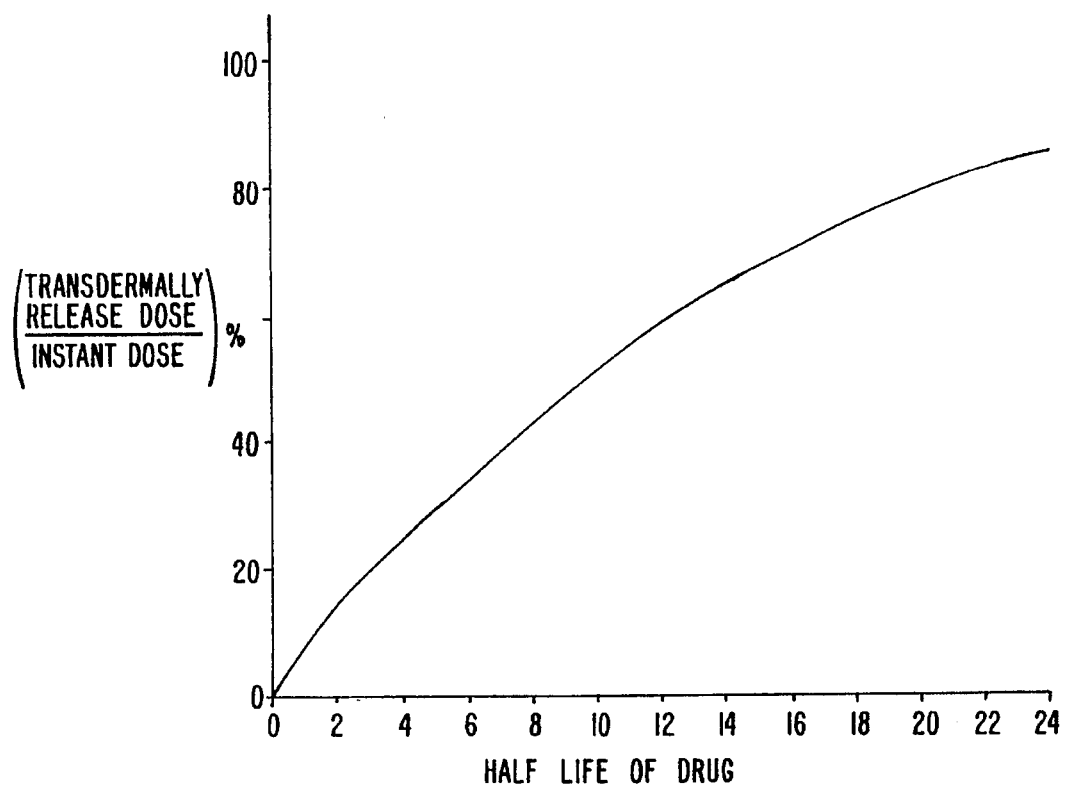
FIG. 1 compares the ratio of drug delivered transdermally (controlled release) to the drug delivered as an instant dose (drug injection) required to achieve 24 hour therapy as a function of the half-life of the drug.
Figure 2:
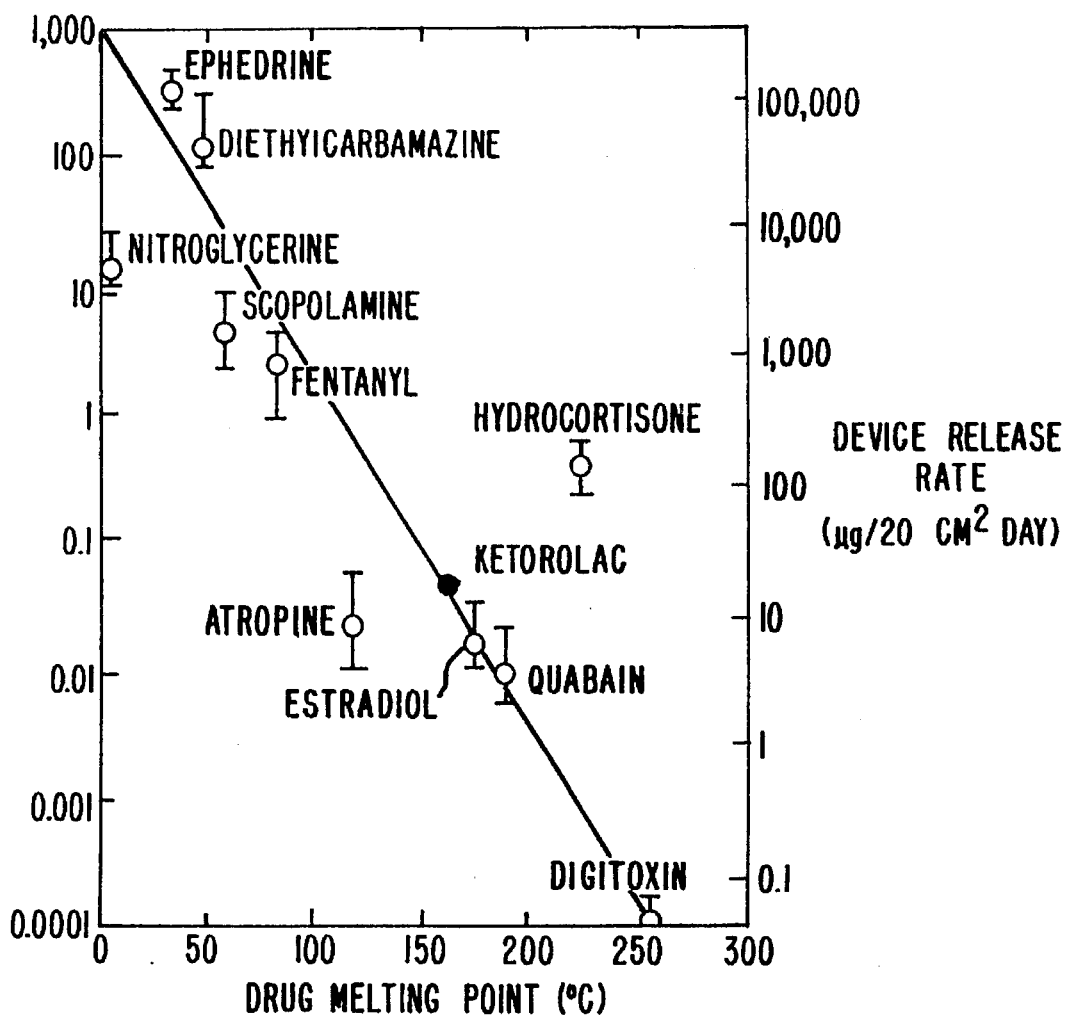
FIG. 2 shows the relationship between the flux rate of various drugs and their melting points.

In describing and claiming the present invention, the term "ketorolac" as used herein refers to any therapeutic form of the analgesic ketorolac including the free acid and its pharmaceutically effective salts, such as hydrochloride, mesylate, hydrobromide, tromethamine, and the like.

The term "(−) ketorolac" as used herein refers to the active enantiomer of ketorolac free acid and its pharmaceutically effective salts, the active enantiomer being substantially free of the inactive enantiomer.

The term "racemic ketorolac" (or the racemate) as used herein refers to the active and inactive enantiomers of ketorolac free acid in combination and their pharmaceutically effective salts.

To date, it has been difficult to transdermally deliver a therapeutically effective dose of ketorolac. This is due primarily to the low flux of ketorolac and the large dose required to attain therapeutic blood levels. The applicants however, have discovered that (−) ketorolac is as permeable to human skin as the racemate. This is an important result because the great majority of the pharmaceutical effect of ketorolac is due to the (−) enantiomer of ketorolac while the (+) enantiomer is relatively ineffective. The use of the (−) enantiomer rather than a racemic mixture thus reduces the amount of drug delivered transdermally that is required to equal the therapeutic effect of the conventional bolus formulation. As described above, approximately 30 to 60 mg/day of the racemic mixture of ketorolac is required to achieve the same therapeutic effect as the bolus injectable dose. The transdermal dose of the racemic mixture requires a delivery rate of about 40 to 80 µg/cm²•hr for a conventional 30 cm² patch. However, transdermal delivery of the (−) enantiomer reduces the required daily dose to 15–30 mg/day or even less. Thus, the required transdermal delivery rate is reduced to 20–40 µg/cm²•hr from a 30 cm² patch.

The ketorolac transdermal patches of the present invention result in a skin flux rate of 40–100 µg/cm²·hr. Thus, they can be used to deliver therapeutically useful amounts of the racemic form of ketorolac. The patches are also suitable for transdermal delivery of the (−) enantiomer of ketorolac which requires a skin flux of approximately 20–40 µg/cm²•hr. The patches of the present invention, for the delivery of both the (−) enantiomer and racemic form of ketorolac, are therapeutically useful at active surface areas of less than 30 cm². As used herein, the term "active surface area" refers to the area of the patch where drug is transmitted to the skin. Accordingly inactive surface area may, for example, be peripheral to the active surface area and may provide an adhesive or structural function.

Ketorolac tromethamine is freely soluble in water and methanol. It has a pKa of 3.54 and a molecular weight of 376.41. The compound is an off-white, crystalline material that melts between 160° C. and 170° C. As such, it is a relatively difficult drug to deliver transdermally because of the extremely lipophilic barrier of the stratum corneum. For adequate skin penetration rates, a chemical enhancer is necessary. There are numerous possible penetration enhancers that can be used such as solvent-type and plasticizing-type enhancers. As used herein, the term "enhancer" is meant to encompass any enhancer or combination of enhancers that increases the permeability of ketorolac to the stratum corneum.

As used herein, "plasticizing-type enhancer" refers to fatty acids and fatty alcohols that are capable of increasing the permeability of drugs to the stratum corneum. A preferred group of plasticizing-type enhancers are fatty acid esters and similar hydrophobic compounds generally having a molecular weight of greater than 150 but less than 300 and having a water solubility of less than 0.5 wt % and preferably 0.2 wt % or less. Without limiting the scope of the present invention, the following is proposed as the mechanism of action of plasticizing-type enhancers. It is believed that the function of these plasticizing enhancers is to migrate into the upper stratum corneum layers of the skin and to remain there for a prolonged period of time. The stratum corneum layer, although only 25–50 microns thick, is the principle barrier to transdermal permeation. The plasticizing enhancers that migrate into the skin serve to increase the mobility and solubility of ketorolac into the skin. To be effective as a plasticizing enhancer, the molecule should be relatively large. In general a molecular weight of approximately 150 is required, or greater than 10 carbon atoms. The plasticizing enhancer must also be relatively water insoluble or it will leach into the subcutaneous tissue layers below the stratum corneum. Thus, plasticizing enhancers with water solubility of less than 0.5 wt % are preferred. It is also preferred that the molecular weight of the plasticizing enhancer be less than 500, because molecules larger than this will have difficulty migrating into the stratum corneum layers.

Fatty alcohols that can be used as plasticizing enhancers include stearyl alcohol and oleyl alcohol. Fatty acids that can be used include oleic acid, lauric acid, myristic acid, palmitic acid, stearic acid, linoleic acid, and palmitoleic acid. Fatty acid esters containing more than 10 to 12 carbons can also be used such as isopropyl myristate and the methyl and ethyl esters of oleic and lauric acid. But many other compounds can also be used such as diethyl hexyl phthalate, octyldodecyl myristate, isostearyl isostearate, caprylic/capric triglyceride, glyceryl oleate, and various oils, such as wintergreen or eucalyptol. Despite these teachings, simple plasticizing enhancers do not sufficiently increase the skin penetration rate of ketorolac to the level required to achieve a therapeutic effect.

As used herein, "solvent-type enhancer" refers to alcohols having molecular weights less than 150 that are capable of increasing the permeability of drugs to the stratum corneum. Solvent type enhancers, which include ethanol, propanol, butanol, benzyl alcohol, glycerin, and propylene glycol, are often better enhancers because they generally provide higher flux rates than plasticizing enhancers. These compounds are all relatively low molecular weight, generally less than 150 in molecular weight. Preferred solvent enhancers have a molecular weight of less than 100. They are also relatively hydrophilic, generally being greater than 2 wt % soluble in water, and are preferably greater than 10 wt % soluble in water. Most preferred solvent enhancers are completely water miscible. While these solvent enhancers can be useful in delivering ketorolac through the skin when used alone, large amounts must be applied continuously to get a prolonged therapeutic effect. As such, they are often irritating to the skin. For example, a 60% aqueous solution of the solvent-type enhancer ethanol is extremely irritating to most patients. For most patients, a 40% aqueous solution is generally acceptable. Unfortunately a 40% solution of ethanol is not a sufficiently powerful enhancer for ketorolac. When a plasticizing type enhancer is used in combination with a solvent type enhancer it is possible to deliver ketorolac through the stratum corneum at therapeutically effective levels. Such a mixture achieves high delivery rates of the drug with relatively dilute solutions of the solvent enhancer. This eliminates the irritation that occurs when solvent-type enhancers solutions are used alone at high concentrations without plasticizing enhancers. When used with plasticizing type enhancers, the function of the solvent enhancer is to rapidly diffuse into the stratum corneum layer of the skin making it possible for the heavier, less mobile plasticizing enhancer to enter the stratum corneum layer. The small size and hydrophilic nature of these solvent enhancers makes them very effective in this role. However, these molecules tend to migrate through the stratum corneum layers and into the subcutaneous tissues very quickly.

In general, the total amount of plasticizing enhancer will be less than the solvent enhancer. For example, a ratio of 1 part plasticizing enhancer to at least 10 parts solvent enhancer is preferred and more preferred is 1 part to 20 or greater parts solvent enhancer. A preferred combination for a reservoir-type device, described in detail below, is 20–60% of a C2–C4 alcohol enhancer, 0.5–20% of a plasticizing type fatty acid ester with the balance being water, glycerine, or propylene glycol. A most preferred combination for a reservoir device is 30–45% ethanol, and 1–5% isopropyl myristate with the balance being water. Ethanol in combination with isopropyl myristate at pH 7 is capable of increasing the skin penetration rate of ketorolac to therapeutically effective levels. This combination is advantageous because the use of a non-acidic enhancer formulation reduces irritation.

Patch Designs

There are several designs of transdermal patches that are commonly used. The particular patch design selected is determined based on a number of factors, one of the more important being the enhancer system. The simplest type of transdermal patch is the adhesive matrix patch where the drug and the enhancer are formulated into the skin adhesive layer. The adhesive layer serves both as the drug and enhancer reservoir as well as the adhesive layer which attaches the patch to the patient's skin. Adhesives by nature are lipophilic being comprised of long chain hydrocarbons. This allows for incorporation of most plasticizing type enhancers which are also typically lipophilic. Because high flux rates of solvent enhancer (on the order of 0.1 mg/cm$^2$•hr or more) are required to achieve therapeutically effective flux rates of ketorolac, it is necessary to formulate patches having in the range of 50–100 mg and more of the solvent enhancer. Only a limited number of the hydrophilic solvent type enhancers typically used for transdermal patches can be formulated at these levels into an adhesive matrix. Solvent type enhancers which can be formulated into an adhesive matrix generally have a boiling point of greater than 100° C. One such enhancer, propylene glycol, is a preferred solvent type enhancer for adhesive matrix patches.

Many of the hydrophilic solvent type enhancers, particularly those having a boiling points of less than 100° C., are not compatible with adhesives. When solvents having a boiling point of less than 100° C. are used, the transdermal patch will generally be a monolithic matrix type or a reservoir type. The monolithic matrix is generally comprised of an impermeable backing layer, a drug depot, a rate-controlling membrane, and an adhesive layer. The drug depot is generally comprised of a non-adhesive type polymer and drug.

A third type of transdermal patch, and the subject of the present invention, is often referred to as a reservoir type transdermal patch. Typically, this type of patch is comprised of an impermeable backing layer which is sealed at its periphery to a rate-controlling membrane layer thus defining a drug depot. The drug depot generally contains the drug, and optionally an enhancer and/or gelling components. An adhesive layer on the rate-controlling membrane attaches the patch to the skin of a patient.

In copending application U.S. Ser. No. 08/470,648, filed Jun. 6, 1995, a number of patch designs of the simple adhesive and monolithic matrix design are described which are capable of delivering the (−) enantiomer of ketorolac at therapeutically useful flux rates of greater than 20 µg/cm$^2$•hr. The design of the reservoir type transdermal patch of the present application is effective in delivering ketorolac at flux rates of greater than 40 µg/cm$^2$/•hr. Thus, the patches of the present invention can be used to deliver either the active enantiomer or the racemic form of ketorolac.

Figure 3:
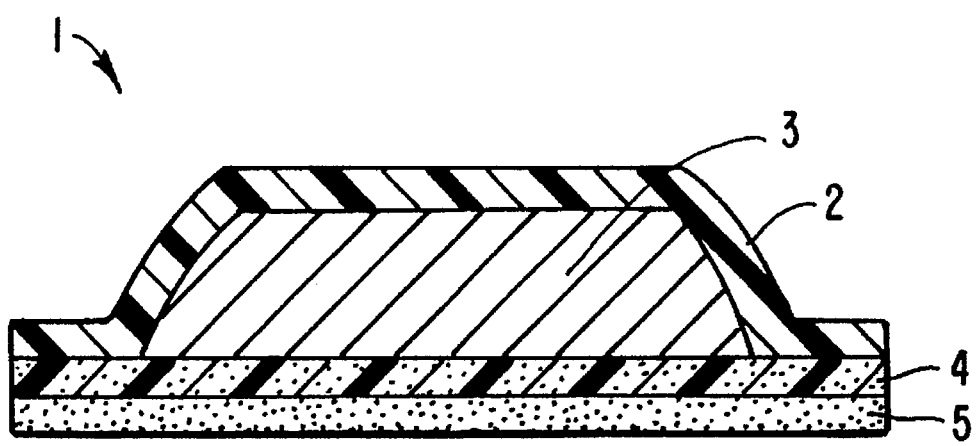
FIG. 3 shows a reservoir type transdermal patch (1) having an impermeable backing (2), a drug depot (3), a porous membrane (4), and an adhesive layer (5). The backing and the porous membrane are sealed at their peripheral edges, thus defining the drug depot.

Looking at the basic embodiment of the present invention as shown in FIG. 3, the ketorolac reservoir type transdermal patch, 1, comprises an impermeable backing layer, 2, and a drug depot (reservoir), 3 (which serves both as a depot for ketorolac and enhancer(s) used), a porous membrane, 4, and an adhesive layer, 5.

The impermeable backing layer, 2, defines the non-skin facing side of the patch in use. The functions of the backing layer are to provide an occlusive layer that prevents loss of ketorolac and the enhancers, in particular the solvent enhancer, to the environment and to protect the patch. The material chosen should exhibit minimal ketorolac and enhancer permeability. The backing layer should be opaque because ketorolac degrades in the presence of light. Ideally, the backing material should be capable of forming a support onto which the ketorolac containing mixture can be cast and to which it will bond securely. Preferred materials are aluminized polyester or polyester medical films available for example from 3M Corporation (Scotchpak® 1005 or 1109).

The membrane layer 4, and backing layer are sealed at their peripheral edges to form the drug reservoir, 3, which contains a solution or gel of the solvent enhancer and drug with plasticizing enhancer. As used herein, the term "peripheral edges" of the membrane and backing layers refers to the areas that are sealed together to define the drug reservoir. Therefore, extraneous membrane and backing layer material may extend outwardly from the drug reservoir and peripheral edge.

The contents of the reservoir, 3, may take various forms, for example, the ketorolac may be dispersed in an enhancer or combination of enhancers, gelled or ungelled. As used herein, the term "dispersed" refers to the distribution of ketorolac throughout the reservoir. The drug may be dispersed in a dissolved and/or undissolved state, but is usually dissolved. Alternatively, the drug/enhancer mixture may be conveniently contained in the pores of a pad or foam material such as a polyurethane foam. The function of the reservoir is to keep the drug and enhancer(s) in good contact with the membrane layer.

The transdermal patch of the present invention differs from the transdermal devices described above in the background section in that the membrane 4, is extremely permeable to the enhancer and the drug contained in the reservoir. Thus the rate of permeation of the enhancer and drug through the membrane is high compared to their permeation rates through the skin. Generally, such a high flux rate of enhancer through the skin causes the skin to become irritated, thus requiring removal of the patch. This irritation problem can be overcome by diluting the enhancer with a non-irritating diluent such as water or other inert compounds such as mineral oil, silicon oil, and the like.

In some cases, when very powerful solvent enhancers are used, the diluted enhancer may be sufficiently effective in enhancing skin permeability to achieve the target flux rate for ketorolac (20–40 µg/cm$^2$•hr for (–) ketorolac; 40–80 µg/cm$^2$•hr for the racemate). Powerful solvent enhancers include N,N dimethylformamide, n-butyl acetate, or ethyl acetate. However, most solvent enhancers, when diluted to the point at which they are no longer irritating, are not effective in enhancing skin permeability to achieve the target flux rate for ketorolac. For example, if the solvent enhancer is ethanol, then a dilution with water to about 40 wt % ethanol is required before it becomes non-irritating; but 40 wt % ethanol is too dilute to achieve therapeutically effective flux rates of ketorolac.

The problem of using dilute solvent enhancers to increase the permeability of skin to ketorolac is overcome when a plasticizing-type enhancer is used in conjunction with the diluted solvent enhancer. When used in conjunction with a plasticizing type enhancer for the transdermal delivery of ketorolac, the solvent enhancer is generally loaded at levels of 2–20 mg/cm$^2$ of patch while much less plasticizing enhancer is used, typically 0.1 to 2 mg/cm$^2$, and more typically 0.5 to 1.0 mg/cm$^2$. The solvent type enhancer must be contained in the reservoir layer of the patch, but the plasticizing enhancer can be placed in the adhesive layer as well as the reservoir layer. The adhesive layer is a preferred location for placing the plasticizing enhancer because it is immediately adjacent to the skin. At this location, the plasticizing enhancer can immediately permeate into the skin producing a rapid enhancement effect. However, it is can also be beneficial to place a portion of the plasticizing enhancer in the reservoir layer along with the solvent to minimize migration of the plasticizing enhancer into the reservoir layer during storage.

The nature of the membrane separating the reservoir from the skin is important. With transdermal devices of the prior art, the membrane layer separating the drug depot from the skin is generally a microporous membrane or a dense polymer film, that is one without a porous network. Dense polymer film can be fabricated from a wide variety of polymers such as ethylene vinyl acetate, silicone rubber, polyolefins, and the like. The polymer is selected based on the intrinsic permeability of the diffusing components in the polymer and the required flux rate of those components. This type of membrane is usually selected when it is desirable to control or limit the release of one of the reservoir compartments. Microporous membranes have a distinct pore structure with pores ranging in diameter from approximately 0.08 to 0.5 microns. Microporous membranes are commonly used in transdermal devices, especially the microporous polyethylene and polypropylene from 3M Company and from Hoechst-Celanese. Microporous membranes are useful when a lesser degree of control over release of the reservoir components is desired.

One would expect a microporous membrane with pores in the range of 0.2 to 0.5 microns to allow for adequate flux of the reservoir components as these pores are much larger than the size of the diffusing solvent and drug molecules. This can be shown with in vitro dissolution tests which reveal that microporous polyethylene releases the contents of the drug reservoir at a rate far higher than the skin's ability to absorb. However, when tested on skin, the flux of the drug is inadequate and below the desired target flux of greater than 40 µg/cm$^2$•hr. It may be that the flux of the solvent enhancer released from the microporous material is impeded due to some effect such as concentration polarization or the overall length to diameter ratio of the microporous membrane along any degree of tortuosity.

The membrane of the present invention is preferably not microporous in nature nor a dense polymer film. The transdermal patches of the present invention are prepared from a porous membrane material. As used herein, the term "porous membrane" refers to a membrane having pores greater than about 3 microns in diameter. Preferred porous membranes have pores greater than about 8 microns in diameter. Such materials are available as woven and non-woven fabrics, such as the non-woven polyester from Dexter Corp. (Windsor Locks, Conn.). These materials can also be fabricated from nylon, polyethylene, and other polyolefins and the like. The improved fluxes provided from this material may be due to a convective wicking action of the fabric and/or to a high length to diameter ratio as these materials have pores in the range of 3–10 microns or more.

The adhesive layer, 5, used in the patch can be selected from a variety of adhesives available commercially and known to those in the art. For example, common adhesives are those based on poly isobutylene, acrylic, and silicone. The selection of the adhesive can be important to the proper functioning of the patch. This is particularly true if an enhancer is placed in the adhesive layer. The adhesive layer must retain its functioning properties in the presence of the enhancer. Often adhesives become stringy and gooey in the presence of the skin permeation enhancers leading to cohesive failure and residual adhesive left on the patient's skin after removal of the patch. In some cases, the patch looses adhesion altogether and falls off. The loss of tack and other adhesion properties generally dictates and limits the amount and type of enhancers that can be loaded into the adhesive matrix type patches. Some acrylate based adhesives, such as those available from Avery and National Starch and Chemical Company, are able to withstand relatively high loadings of enhancers, both solvent-type and plasticizing type.

The liquid reservoir patch of the present invention will be useful in the transdermal delivery of other drugs (in addition to ketorolac) which require high flux rates of a solvent type enhancer to achieve a therapeutic effect.

The invention is now further illustrated by Examples 1 to 3 which are exemplary but not scope-limiting.

Measurement of skin permeation rates

EXAMPLE 1

Skin permeation rates of various ketorolac/enhancer formulations were determined using flow through diffusion cells with an active area of 1 cm$^2$ and a receiving volume of 3 ml. The receptor fluid, isotonic saline, was pumped into and through the cells by a peristaltic pump. Samples were collected in glass vials arranged in an automatic fraction collector. Human skin was placed on the lower half of the diffusion cell with the stratum corneum facing the donor compartment. The test solution or transdermal device was placed on the stratum corneum and the amount of drug permeated across the skin (µg/c$^2$·hr) was calculated from the cumulative release.

Preparation of ketorolac reservoir patches

EXAMPLE 2

An acrylate adhesive casting solution is prepared containing 30% isopropyl myristate. The casting solution is cast onto a polyester film (3M #1022) with a 750 μm knife and dried at room temperature for 30 minutes and then at 100° C. for 15 minutes. A non-woven polyester membrane (Dexter Corp. #9770) is laminated to the resulting adhesive film. This three layer assembly is peripherally heat sealed to Scotchpak backing #1009, leaving a small opening in the heat seal to fill the reservoir. Patches are punched out by cutting along the outer edge of the heat seal. The reservoir of the patch is filled with a 24% (−) ketorolac tromethamine solution in 37% ethanol, 35% water, 1.1% isopropyl myristate and 0.4% hydroxy propyl cellulose. The opening in the heat seal by which the fill solution is introduced is sealed after filling.

Preparation of ketorolac reservoir patches with foam

EXAMPLE 3

An acrylate adhesive casting solution is prepared including 30% isopropyl myristate. The casting solution is cast onto a polyester film (3M #1022) and dried at room temperature for 30 minutes and then at 100° C. for 15 minutes. A nonwoven polyester material (Dexter Corp. #9770) is laminated to the resulting adhesive film. This three layer assembly was peripherally heat sealed to ⅛ inch thick polyurethane foam (from Foamex Corp.) and a backing material (3M Corp, X-21220). The foam reservoir is filled with a 24% ketorolac tromethamine solution in 37% ethanol, 37% water, 1.1% isopropyl myristate and 0.4% hydroxy propyl cellulose. The opening in the heat seal by which the fill solution is introduced is sealed after filling and the patches are tested in vitro as described in Example 1.

What is claimed is:

1. A patch for the transdermal administration of ketorolac through a patient's skin for a period of 12 hours or more, said patch comprising:
   (a) an occlusive backing layer having a skin-facing side and a peripheral edge,
   (b) a porous membrane having a skin-facing side and a peripheral edge sealed to said peripheral edge of said backing layer and defining a drug depot therebetween, and
   (c) said drug depot comprising:
      i. ketorolac, and
      ii. an enhancer combination in which said ketorolac is dispersed, said enhancer combination comprising a first portion of a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and
   (d) an adhesive layer comprising an adhesive and a second portion of said plasticizing-type enhancer, said adhesive layer being in contact with said skin-facing side of said porous membrane, wherein said patch delivers ketorolac through the skin facing side of said patch and through said patient's skin at a flux rate of about 40 μg/cm$^2$·hr or more.

2. The patch of claim 1 wherein said plasticizing-type enhancer is isopropyl myristate.

3. The patch of claim 1 wherein said solvent-type enhancer is ethanol.

4. The patch of claim 1 wherein said depot further comprises:
   iii. a foam material, said ketorolac and said enhancer being contained in said foam material.

5. The patch of claim 1 wherein said porous membrane has pores greater than 8 microns in diameter.

6. A patch for the transdermal administration of (−) ketorolac through a patient's skin for a period of 12 hours or more, said patch comprising:
   (a) an occlusive backing layer having a skin-facing side and a peripheral edge,
   (b) a porous membrane having a skin-facing side and a peripheral edge sealed to said peripheral edge of said backing layer and defining a drug depot therebetween, and,
   (c) said drug depot comprising:
      i. ketorolac, and
      ii. an enhancer combination in which said ketorolac is dispersed, said enhancer combination comprising a first portion of a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and
   (d) an adhesive layer comprising an adhesive and a second portion of said plasticizing-type enhancer, said adhesive layer being in contact with said skin-facing side of said porous membrane, wherein said patch delivers (−) ketorolac through the skin facing side of said patch and through said patient's skin at a flux rate of about 20 μg/cm$^2$·hr or more.

7. The patch of claim 6 wherein said plasticizing-type enhancer is isopropyl myristate.

8. The patch of claim 6 wherein said solvent-type enhancer is ethanol.

9. The patch of claim 6 wherein said depot further comprises:
   iii. a foam material, said ketorolac and said enhancer being contained in said foam material.

10. The patch of claim 6 wherein said porous membrane has pores greater than 8 microns in diameter.

11. A method of administering ketorolac to a patient in need of such administration, comprising:
    (a) applying to the skin of said patient a transdermal patch having a skin-facing side, said patch comprising:
       i. an occlusive backing layer having a skin-facing side, and
       ii. means defining a drug depot having a skin-distal side in contact with said skin-facing side of said backing layer, said drug depot containing ketorolac and an enhancer combination comprising a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and (b) delivering ketorolac through the skin-facing side of said patch and through said patient's skin at a flux rate of about 40 µg/cm²·hr or more.

12. The method of claim 11 wherein said patch has an active surface area of less than 30 cm².

13. The method of claim 11 wherein less than 60 mg of ketorolac is delivered to said patient over a 24 hour period.

14. A method of administering ketorolac to a patient in need of such administration, comprising:

(a) applying to the skin of said patient a transdermal patch having a skin-facing side, said patch comprising:
  i. an occlusive backing layer having a skin-facing side, and
  ii. means defining a drug depot having a skin-distal side in contact with said skin-facing side of said backing layer, said drug depot containing (−) ketorolac and an enhancer combination comprising a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and (b) delivering (−) ketorolac through the skin facing side of said patch and through said patient's skin at a flux rate of about 20 µg/cm²·hr or more.

15. The method of claim 14 wherein said patch has an active surface area of less than 30 cm².

16. The method of claim 14 wherein less than 30 mg of (−) ketorolac is delivered to said patient over a 24 hour period.

* * * * *